(12) United States Patent
Martens et al.

(10) Patent No.: US 7,008,775 B2
(45) Date of Patent: Mar. 7, 2006

(54) DIAGNOSTIC METHOD FOR SCREENING COMPLEMENT REGULATORY PROTEIN LEVELS TO PREDICT SPONTANEOUS ABORTION

(76) Inventors: Mark G. Martens, 12217 S. Ash Ave., Jenks, OK (US) 74037; Anil K. Kaul, 3340 Queensland La., Plymouth, MN (US) 55447; Rashmi Kaul, 3340 Queensland La., Plymouth, MN (US) 55447

( * ) Notice: Subject to any disclaimer, the term of this patent is extended or adjusted under 35 U.S.C. 154(b) by 0 days.

(21) Appl. No.: 10/291,992

(22) Filed: Nov. 12, 2002

(65) Prior Publication Data

US 2003/0129674 A1 Jul. 10, 2003

Related U.S. Application Data

(63) Continuation of application No. PCT/US01/14768, filed on May 9, 2001.

(60) Provisional application No. 60/204,344, filed on May 15, 2000.

(51) Int. Cl.
  *G01N 33/53* (2006.01)
(52) U.S. Cl. ................ 435/7.1; 435/7.2; 435/91.1; 435/92.1; 436/510; 436/517; 436/65
(58) Field of Classification Search ................ 435/7.1, 435/7.2, 91.1, 92.1; 436/510, 517, 65
  See application file for complete search history.

(56) References Cited

U.S. PATENT DOCUMENTS 5,376,531 A * 12/1994 Anderson et al. .......... 435/7.23

FOREIGN PATENT DOCUMENTS

JP   200002703   *  6/1998

OTHER PUBLICATIONS

Cunningham et al. Clinical Immunology and Immunopathology 1995 74: 156-161.*
Bjorge, L..,et al. ,"Soluble CD59 in Pregancy and Infancy", *Immunology Letters, 36*, Letter to the Editor,(1993),p. 233.
Holmes, C..H. ,et al. ,"Complement and Pregancy: New Insights into the Immunobiology of the Fetomaternal Relationship", *Baillieres's Clinical Obstetrics and Gynecology, 6*, (1992),439-460.
Holmes, C..H. ,et al. ,"Complement Regulatory Proteins at the Feto-maternal Interface During Human Placental Development: Distribution of CD59 by Comparison with Membrane Cofactor Protein (CD46) and Decay Accelerating Factor (CD55)", *Eur. J. Immunology, 22*, (1992), 1579-1585.
Imrie, H..J. ,et al. ,"Reduction in Erythrocyte Complement Receptor 1 (CR1, CD35) and Decay Accelerating Factor (DAF, CD55) During Normal Pregnancy", *Journal of Reproductive Immunology, 31*, (1996),221-227.
McLaughlin, P..J. ,et al. ,"Soluble CD46 (Membrane Cofactor Protein, MCP) in Human Reproductive Tract Fluids", *Journal of Reproductive Immunology, 31*, (1996),209-219.
Morgan, B..P. ,"Physiology and Pathophysiology of Complement: Progress and Trends", *Critical Reviews in Clinical Laboratory Sciences, 32*, (1995),265-298.
Vanderpuye, O..A. ,et al. ,"Characterization of Cofactor Activity for Factor I: Cleavage of Complement C4 in Human Syncytiotrophoblast Microvilli", *Placenta, 15*, (1994), 157-170.

* cited by examiner

Primary Examiner—Long V. Le
Assistant Examiner—Jacob J. Cheu
(74) Attorney, Agent, or Firm—Schwegman, Lundberg, Woessner & Kluth, P.A.

(57) ABSTRACT

The invention provides a method for the early detection of pregnancy failure, spontaneous abortion or premature birth by determinations of complement regulatory protein levels. A kit for use in rapid identification of these pregnancy complications is also provided.

12 Claims, 2 Drawing Sheets

DIAGNOSTIC METHOD FOR SCREENING COMPLEMENT REGULATORY PROTEIN LEVELS TO PREDICT SPONTANEOUS ABORTION

CROSS-REFERENCE TO RELATED APPLICATIONS

This application is a continuation of PCT/US01/14768, filed on May 9, 2001, which claimed priority under 35 U.S.C. 119(e) of U.S. Provisional Application Ser. No.: 60/204,344, filed May 15, 2000, which applications are incorporated herein by reference.

BACKGROUND OF THE INVENTION

Twelve to twenty-two percent of all pregnancies end in spontaneous abortion, or miscarriage. Most data available suggest genetic, hormonal or immunological factors associated with a majority of spontaneous abortions. About 40% of all miscarriages are estimated to be the result of chromosomal abnormalities. Various hypotheses have been proposed for the remaining 60%, and a variety of tests and therapies have been proposed for diagnosing and treating high-risk pregnancy. For example, high-risk pregnancies are evaluated using Doppler evaluation of uterine artery blood flow (Caforio, L. et al., *Fetal Diagn. Ther.* (1999) 14: 201–5), screening for and measurement of anti-paternal antibodies (Orgad, S., et al. *Hum. Reprod.* (1999) December 14: 2974–9), and measurement of MSAFP (maternal serum alpha-fetoprotein) levels, among others.

Despite the application of currently available technologies for screening high-risk pregnancies, reliable methods have not been found. The pathology of spontaneous abortion is difficult to elucidate. Immunologically, a fetus is a semi-allogenic graft and blunting of the immune system is required to permit maintenance of the fetus by the mother. Some have suggested that anti-paternal antibodies cause rejection of the fetus by the maternal immune system, and one treatment that has been proposed for recurrent miscarriage is intravenous immunoglobulin therapy (Daya, S., et al., *Hum. Reprod. Update* (1999) 5: 475–82). Others have suggested that maternal blood flow to the placenta contributes to spontaneous abortion pathology.

One hypothesis that has been suggested for spontaneous abortion pathology is maternal rejection of the fetus due to complement regulatory proteins at the feto-maternal interface. Although one group has recently described a cell surface protein in mice that is directly involved in fetal survival (Xu, et al., *Science* (2000) 287:498–501), no such molecule has been described in humans.

Differential expression of complement regulatory proteins at the feto-maternal interface was investigated in 1992 by Holmes, et al. (Holmes, C. H., et al., Eur. J. Immunol. (1992) 22: 1579–85), who suggested that differential expression might reflect the need for specific functional activities within the placenta, and that these proteins might be involved in pregnancy pathologies (Holmes, C. H., et al. (1992) *Baillieres Clin. Obstet. Gynaecol.* 6: 439–60). Fenichel et al. investigated complement regulatory proteins on human sperm, unfertilized oocytes, and pre-implantation embryos, concluding that selective expression of complement regulatory proteins associated with a lack of MHC class I antigens might represent an immune protective mechanism for gametes and pre-implantation embryos during their travel through the female genital tract (Fenichel, P., et al., *Contracept. Fertil. Sex* (1995) 23: 576–80).

Pinpointing the pathologic mechanism and devising an accurate screening technique for high-risk pregnancy has, however, been complicated by the complexity of the human immune and reproductive systems. For example, Imrie et al. suggested that reduction in CD35 (CR1) and CD55 (DAF) reflect increased levels of circulating immune complexes and consequent increased complement activation in pregnancy—an outcome that would appear to put the fetus at risk in normal pregnancy, if complement activation is part of the pathology of spontaneous abortion (Imrie, H. J., et al. *J. Reprod. Immunol.* (1996) 31: 22114 7). And, although the mouse model has provided valuable insights into mechanisms of immune response, there are fetomaternal tolerance mechanisms that are quite different between humans and mice, making extrapolation from the mouse model to the human system problematic. For example, the Crry gene demonstrated by Xu et al. to determine fetal survival in mice is absent in humans.

While pathologic mechanisms associated with spontaneous abortion remain unclear, there remains a need for a simple and effective screening method for identifying high-risk pregnancies.

SUMMARY OF THE INVENTION

The present invention provides a method for diagnosing a predisposition for pregnancy failure, spontaneous abortion or premature birth in a pregnant patient by contacting a physiological fluid potentially comprising a cell membrane-associated complement regulatory protein (CRP) from the patient with a anti-CRP antibody to form an CRP-antibody complex; and measuring the quantity of CRP-antibody complex in the physiological fluid as compared to a normal control level, wherein the quantity of CRP-antibody complex as compared to the normal control is indicative for a predisposition for pregnancy failure, spontaneous abortion or premature birth. The CRP may be CD35 (complement receptor type 1, CR1), CD46 (membrane cofactor protein, MCP), CD55 (also decay accelerating factor, DAF) or CD59 (membrane attack complex inhibitory factor, MACIF). The anti-CRP antibody may be immobilized on a solid surface. The anti-CRP antibody may be a detectable label or a binding site for a detectable label to form detectable complexes. The detectable label may be an enzyme label, or a fluorogenic compound. The binding site for the detectable label may be biotin, avidin or streptavidin.

The present invention also provides a method for diagnosing a predisposition for pregnancy failure, spontaneous abortion or premature birth in a pregnant patient by contacting a physiological fluid from the patient, wherein the fluid potentially comprises CRP, with a solid surface having immobilized thereon anti-CRP antibodies, so that the CRP binds to the anti-CRP antibodies; contacting labelled CRP, which comprises a detectable label or a binding site for a detectable label, with the solid surface, so that the labelled CRP binds to free antibodies on the solid surface to form detectable complexes; and detecting the complexes, wherein the quantity of the complexes is inversely proportional to the amount of CRP in the physiological fluid, wherein the quantity of CRP-antibody complex as compared to a normal control is indicative for a predisposition for pregnancy failure, spontaneous abortion or premature birth. The CRP may be CD35, CD46, CD55 or CD59. The detectable label may be an enzyme label or a fluorogenic compound. The binding site for the detectable label may be biotin, avidin or streptavidin.

The present invention also provides an article of manufacture for diagnosing a predisposition for pregnancy failure, spontaneous abortion or premature birth in a pregnant patient comprising packaging material, and a diagnostic kit and instructions within the packaging material, wherein the diagnostic kit comprises anti-CRP antibody, and a means for measuring the quantity of CRP-antibody complexes in a physiological fluid from a patient, wherein the quantity of CRP-antibody complex as compared to a normal control is indicative for a predisposition for pregnancy failure, spontaneous abortion or premature birth, and wherein the instructions that indicate that the diagnostic kit can be used to diagnose a predisposition for pregnancy failure, spontaneous abortion or premature birth in a pregnant patient. The CRP may be CD35, CD46, CD55 or CD59. The kit may also contain a solid substrate. The anti-CRP antibody of the kit may be immobilized on a solid surface. The anti-CRP antibody may be a detectable label or a binding site for a detectable label to form detectable complexes. The detectable label may be an enzyme label. The detectable label may be a fluorogenic compound. Alternatively, the binding site for the detectable label may be biotin, avidin or streptavidin.

DETAILED DESCRIPTION

Figure 1:
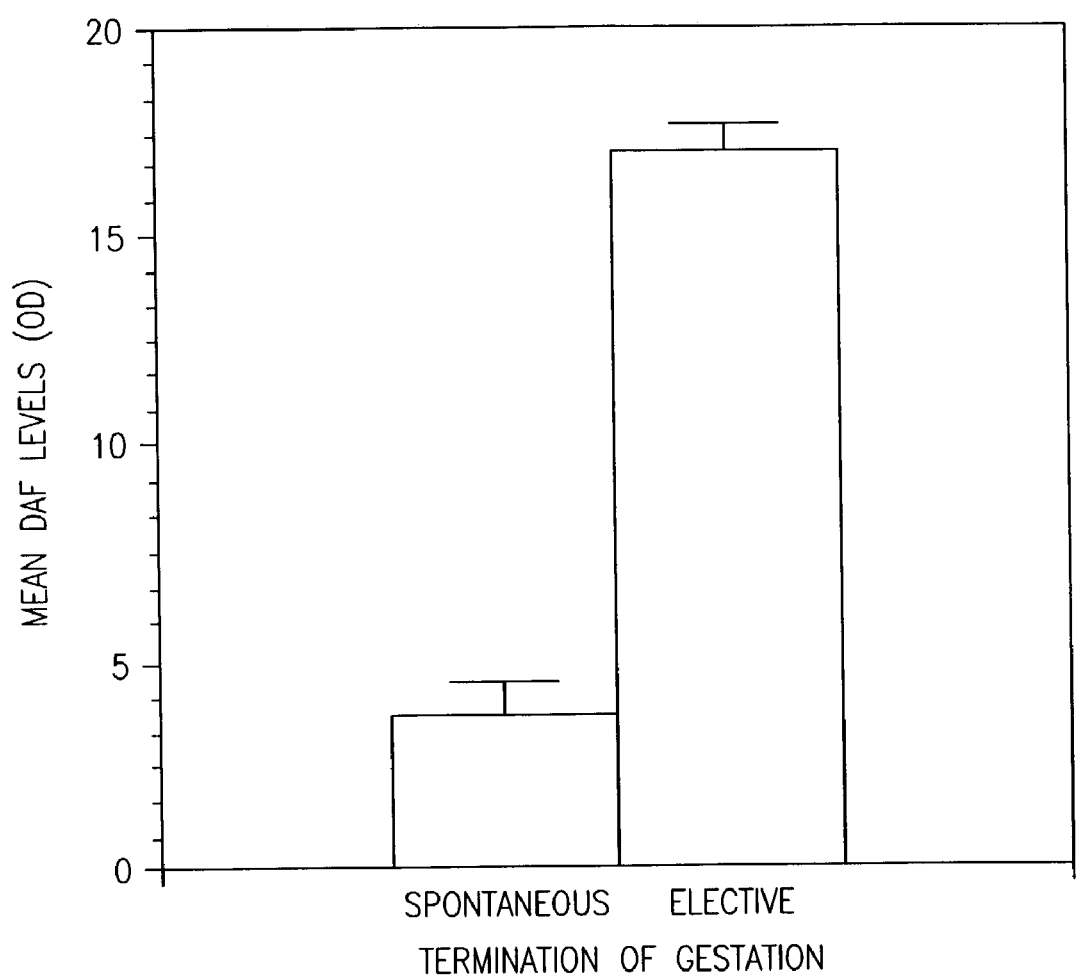
FIG. 1: Graph comparing endometrial DAF levels from women having spontaneous or elective terminations of pregnancy. The range of DAF level for elective terminations were from 11–35, whereas the DAF levels for spontaneous abortions were from 0–13.9. Thus, the mean for elective terminations was at 16.9, whereas the mean for spontaneous terminations was at 3.6. These data give a statistically significant P value of less than 0.0001.
Figure 2:
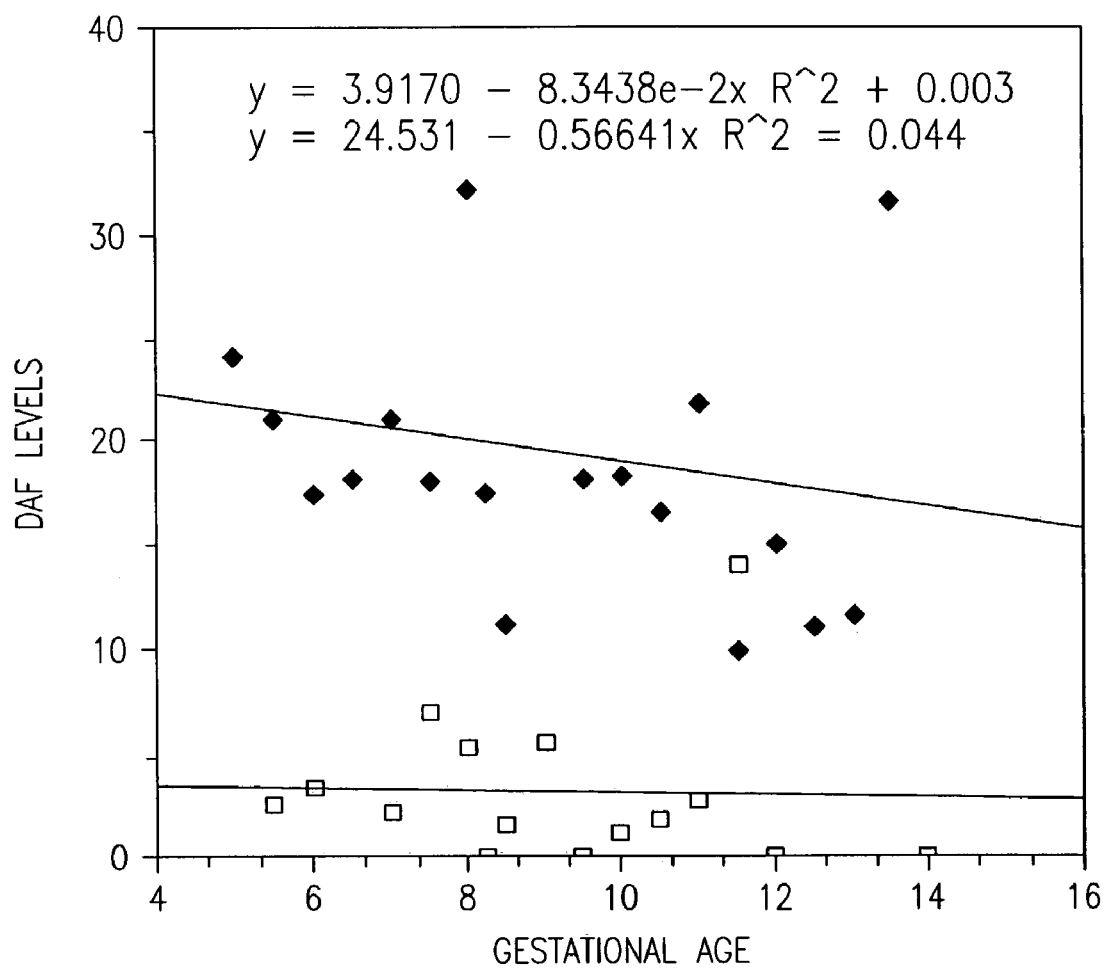
FIG. 2: Graph comparing DAF in spontaneous and elective abortions. The levels of DAF vary depending on whether pregnancy is viable or miscarried. Levels below 10 are consistently found in spontaneously aborted pregnancies, which is predictive of which pregnancies will spontaneously abort.

The present invention provides a method for screening for high-risk pregnancies. The inventors have identified a cell-associated complement-regulatory protein, the levels of which are correlated with the occurrence of pregnancy failure, including spontaneous abortion and premature birth. Premature birth is generally defined as delivery between the point of viability (about 22 weeks of gestation) and about 33 weeks of gestation. Premature birth is associated with increased perinatal mortality and morbidity. Early detection of premature birth can delay labor long enough to permit effective preventive measures. Spontaneous abortion (miscarriage) is generally defined as a non-elective termination of pregnancy before the point of viability. A method is provided for quantifying levels of the complement-regulatory protein, and thereby identifying women who are at-risk for pregnancy failure, spontaneous abortion or premature birth.

The present invention provides a method for determining the presence or the level of CRP in a biological sample containing CRP. For example, decay accelerating factor (DAF, CD55) is a cell-associated complement-regulatory protein that inhibits complement activation and thus protects the autologous tissues from the cytotoxic effects of complement. DAF has been previously associated with paroxysmal nocturnal hemobloginuria (PNH), as decreased expression of DAF is correlated with presence of the disease. However, PNH is characterized, in part, by lysis of red blood cells (RBCs), and it has been shown that RBCs which do not express DAF (Inab phenotype) often survive complement attack and lysis.

DAF is associated with the Cromer blood group antigens, which are located at various positions along the DAF molecule. It has been characterized as a glycosylphosphatidylinositol (GPI)-anchored membrane protein that inhibits both the classical and alternative pathways of complement activation, its chromosomal location has been identified as band q32.8,9 of human chromosome 1, and its sequence has been reported (Medof, M. E., et al. *Proc. Natl. Acad. Sci. USA* (1987) 84: 2007–11). In conjunction with CD59 (protectin), CD46 (membrane cofactor protein), and CD35 (complement receptor type 1 (CR1)), it participates in the regulation of complement activity in the immune response.

The inventors have determined that DAF levels are useful for predicting the risk of spontaneous abortion in pregnant women. The method for screening for high-risk pregnancy is described briefly as follows. Urine, serum and/or saliva samples are collected from the patient and are appropriately diluted, such as at a 1:10 to 1:100 level, in an appropriate buffer, such as PBS/BSA 1%, Tween 20 buffer. Serial dilutions of recombinant DAF can be used as a control standard. Microtiter plates are coated with an appropriate amount of anti-human DAF antibody in an appropriate buffer, such as 2.5 $\mu$g/ml purified anti-human DAF antibody (CD55, Clone IA10, Pharmingen, San Diego, Calif.) in NaHCO$_3$ buffer, pH 8.2. After incubation, the plates are washed and blocked, such as with 2% BSA in PBS. The samples are added to the plates and incubated, such as for about 1.5 hours at room temperature. The plates were washed again, and biotynalated anti-human DAF is added and incubated. After another washing step, streptavidin peroxidase was added and incubated. The reaction was developed by adding diaminobenzidine (DAB). Plates were read in an ELISA reader and concentration of unknowns were calibrated against the serial dilutions of recombinant DAF standard. OD levels below about 14 are at risk for a spontaneous abortion. In particular, OD levels below about 10 are consistently found in spontaneously aborted pregnancies.

Immunoassays

Examples of immunoassays that can be employed to determine the relative or absolute amount of CRP in a biological sample include those assay methods, formats and kits disclosed in U.S. Pat. No. 5,516,639. CRP analytes may be distinguished from other sample components by reacting the analyte with a specific receptor for that analyte. Assays that utilize specific receptors to distinguish and quantify analytes are often called specific binding assays. The analyte of the present invention may be detected using a variety of specific binding assay formats. For example, various direct-binding assays may be employed. In such assays, receptors, such as antibodies or other binding proteins, are chemically coupled to make a cross-linked protein complex and the complex is immobilized on a solid phase. The immobilized chemically cross-linked protein complexes are contacted with a sample containing the analyte of interest, which may be distinguished from other components found in the sample. For example, an antibody specific for a CRP can be immobilized on the surface of a solid substrate and used as a capture antibody to specifically bind to CRP in a biological fluid. Suitable substrates include particulate substrates such as polystyrene beads, the wells of plastic microtiter plates, paper or synthetic fiber test strips and the like. The immobilized antibody can then be contacted with the test sample to be assayed, e.g., with a biological fluid such as plasma, serum, tears, urine or the like. The resulting antibody-CRP binary complex can then be contacted with an anti-CRP antibody, such as rabbit anti-CRP serum.

Following binding of the analyte by the immobilized complex, the solid phase may be washed and then contacted with an indicator, such as a labeled conjugate. The conjugate comprises an antibody, antibody fragment, binding protein or analyte depending on assay format, and the label is a florescent, enzymatic, colorimetric, radiometric or other labeling molecule that is associated either directly or indirectly with the conjugate. The label may be comprised of an enzymatic compound that produces florescence upon contact with a substrate. The extent to which the indicator is present on the solid support can be correlated with the amount of unknown analyte (see, for example, Tijssen, P., *Laboratory Techniques in Biochemistry and Molecular Biology*, Practice and Theory of Enzyme Immunoassay, pp. 173–219 (Chapter 10) and pp. 329–384 (Chapter 14), Elsevier Science Publishers, Amsterdam, The Netherlands, (1985)).

An anti-CRP monoclonal antibody can be itself coupled to a detectable label of a binding site for a detectable label. For example, the antibodies can be labeled radioisotopically, e.g., by $^{125}$I, or conjugated directly to a detector enzyme, e.g., alkaline phosphatase or horse radish peroxidase, or can be labeled indirectly with a binding site for a detectable label, e.g., via biotinylation. The biotinylated antibody can then be detected by its ability to bind to a an avidin-linked enzyme. If the second antibody is biotinylated, a detector enzyme conjugated to avidin will be subsequently added. The final step for detecting enzymes conjugated to monoclonal antibody or to avidin its the addition of a substrate appropriate for the enzyme to allow quantitative colorimetric detection of reaction product. The value (read in optical density units) can be converted to fmol of CRP by reference to a standard curve generated in a control assay in which a standard extract of detergent-solubilized CRP is added in graded concentrations to the immobilized anti-CRP monoclonal antibody.

The present invention may use many other assay formats, such as competitive immunoassays, bead agglomeration assays and sandwich-type immunoassays, such as ELISA, as would be recognized by the art.

In competitive assay formats, the solid phase containing immobilized chemically cross-linked protein complexes with specificity for a selected analyte is contacted with a sample presumably containing such analyte and with a specific competitive reagent. The specific competitive reagent may be a labeled analog of the analyte. In this specific embodiment, the labeled analog competes with the sample analyte for binding to a receptor immobilized on the solid phase.

In the alternative, an analyte may be coupled to a solid phase and contacted with a sample and with a specific competitive cross-linked protein reagent, for example, a labeled receptor for the analyte. In this format, sample analyte competes with solid phase analyte for binding with soluble labeled cross-linked receptor. In both embodiments, the amount of label bound to the solid phase after washing provides an indication of the levels of analyte in the sample. That is, the amount of analyte in a sample is inversely proportional to the amount of analyte in the sample.

Another embodiment of the present invention is a diagnostic kit for detecting or determining the presence of CRP in a biological sample. Immobilized antibodies and labeled antibodies are conveniently packaged in kit form, wherein two or more of the various immunoreagents will be separately packaged in preselected amounts, within the outer packaging of the kit, which may be a box, envelope, or the like. The packaging also preferably comprises instruction means, such as a printed insert, a label, a tag, a cassette tape and the like, instructing the user in the practice of the assay format.

For example, one such diagnostic kit for detecting or determining the presence of CRP comprises packaging containing, separately packaged: (a) a solid surface, such as a fibrous test strip, a multi-well microliter plate, a test tube, or beads, having bound thereto antibodies to CRP; and (b) a known amount of antibodies specific to CRP, wherein said antibodies comprise a detectable label, or a binding site for a detectable label.

In one embodiment of the invention, a clinical test kit is supplied for use in a hospital or clinic. Such a kit consists, for example, of a microtiter plate that is coated with an appropriate amount of anti-human DAF antibody and purified anti-human DAF antibody. Appropriate buffers may also be provided. Further, streptavidin peroxidase and diaminobenzidine (DAB) may be provided. When provided to a qualified technician or other health care worker in a hospital or clinic, the kit provides a method for assaying DAF levels from a sample supplied by a patient who may or not be at risk for spontaneous abortion or miscarriage. By analyzing the levels of DAF in the sample, it is possible to identify increased risk of miscarriage and to provide appropriate treatment and counseling.

Solid Supports

A solid support useful in the present invention is a matrix of material in a substantially fixed arrangement. Exemplary solid supports include glasses, plastics, polymers, metals, metalloids, ceramics, organics, etc. Solid supports can be flat or planar, or can have substantially different conformations. For example, the substrate can exist as particles, beads, strands, precipitates, gels, sheets, tubing, spheres, containers, capillaries, pads, slices, films, plates, slides, etc. Magnetic beads or particles, such as magnetic latex beads and iron oxide particles, are examples of solid substrates that can be used in the methods of the invention. Magnetic particles are described in, for example, U.S. Pat. No. 4,672,040, and are commercially available from, for example, PerSeptive Biosystems, Inc. (Framingham Mass.), Ciba Corning (Medfield Mass.), Bangs Laboratories (Carmel Ind.), and BioQuest, Inc. (Atkinson N.H.).

Indicator Labels

The labels used in the assays of invention can be primary labels (where the label comprises an element which is detected directly) or secondary labels (where the detected label binds to a primary label, e.g., as is common in immunological labeling). An introduction to labels, labeling procedures and detection of labels is found in Polak and Van Noorden (1997) *Introduction to Immunocytochemistry*, second edition, Springer Verlag, N.Y. and in Haugland (1996) *Handbook of Fluorescent Probes and Research Chemicals*, a combined handbook and catalogue Published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetramethylrhodamine isothiocyanate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P), enzymes (e.g., horse-radish peroxidase, alkaline phosphatase) spectral colorimetric labels such as colloidal gold or colored glass or plastic (e.g. polystyrene, polypropylene, latex) beads. The label may be coupled directly or indirectly to a component of the detection assay (e.g., the labeling nucleic acid) according to methods well known in the art. As indicated above, a wide variety of labels may be used, with the choice of label depending on sensitivity required, ease of conjugation with the compound, stability requirements, available instrumentation, and disposal provisions. In general, a detector which monitors an analyte-receptor complex is adapted to the particular label which is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound analyte is digitized for subsequent computer analysis.

Preferred labels include those which utilize 1) chemiluminescence (using Horseradish Peroxidase and/or Alkaline Phosphatase with substrates that produce photons as breakdown products) with kits being available, e.g., from Molecular Probes, Amersham, Boehringer-Mannheim, and Life Technologies/Gibco BRL; 2) color production (using both Horseradish Peroxidase and/or Alkaline Phosphatase with substrates that produce a colored precipitate) (kits available from Life Technologies/Gibco BRL, and Boehringer-Mannheim); 3) hemifluorescence using, e.g., Alkaline Phosphatase and the substrate AttoPhos (Amersham) or other substrates that produce fluorescent products, 4) Fluorescence (e.g., using Cy-5 (Amersham), fluorescein, and other fluorescent tags); 5) radioactivity using kinase enzymes or other approaches. Other methods for labeling and detection will be readily apparent to one skilled in the art.

Fluorescent labels are highly preferred labels, having the advantage of requiring fewer precautions in handling, and being amendable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Fluorescent moieties, which are incorporated into the labels of the invention, are generally are known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent tags are commercially available from the SIGMA Chemical Company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka ChemicaBiochemika Analytika (Fluka Chemie AG, Buchs, Switzerland), and Applied Biosystems (Foster City, Calif.), as well as many other commercial sources known to one of skill.

Most typically, the analyte is measured by quantifying the amount of label fixed to the solid support by the capture of the linked complex between analyte and receptor. Typically, the presence in the reaction mixture of an analyte-receptor complex will increase or decrease the amount of label fixed to the solid support relative to a control reaction which does not comprise the analyte. Means of detecting and quantifying labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems which are widely available.

Biological Samples

Biological samples that can be used in the present invention include physiological fluids. Physiological fluids from patients include plasma, serum, tears, urine, and the like.

The following examples are intended to illustrate but not limit the invention.

EXAMPLES

Example 1

Estimation of DAF in Biological Fluids by ELISA

Levels of DAF in the urine, serum and saliva obtained from patients was determined by Enzyme linked immunoabsorbent assay (ELISA). Flat bottomed, 96-well microtiter plates (Immunolon I, Dynatech Labs, Chantilly, Va.) were coated with 2.5 µg/ml purified anti-human DAF antibody (CD55, Clone IA10, Pharmingen, San Diego, Calif.) in NaHCO$_3$ buffer, pH 8.2. The plates were washed three times after overnight incubation at 4° C. and blocked for 2 hours at 37° C. with 2% BSA in PBS. Serial dilutions of recombinant DAF were used as standard. Urine and saliva samples were diluted at 1:10, and serum samples at 1:100 in PBS/BSA 1%, Tween 20 buffer and were incubated in plates for 1.5 hours at room temperature. Plates were washed again three times as above. Biotynalated anti-human DAF (CD55, Clone IA10, Pharmingen, San Diego, Calif.) diluted in PBS was added and incubated for another hour. After another washing step as above, streptavidin peroxidase was added and incubated for 30 minutes. The reaction was developed by adding diaminobenzidine (DAB) (Sigma, St. Louis, Mo.). Plates were read in an ELISA reader and concentration of unknowns were calibrated against the serial dilutions of recombinant DAF standard.

Example 2

Determination of Levels of Endometrial DAF

Endometrial samples were obtained from 51 pregnant women, including 34 undergoing elective and 17 undergoing spontaneous abortions. Six micrometer sections were stained with anti-human DAF IgG by immunohistochemistry. DAF expression was quantitated by a computer-based image analysis system. The relative increase in the OD value was calculated as percent of increase in cumulative OD values. The baseline was measured in a parallel section where buffer replaced the antibody.

The relative increase in integrated optical-density of DAF in the endometrial tissue of patients undergoing spontaneous abortions was 2.7% (n=17). The density of DAF expression was substantially increased to 16.75% ($p<0.0001$) in the endometrium of patients undergoing elective termination of pregnancy (n=34). About 97% of pregnancies with endometrial DAF level lower than 10% terminated spontaneously.

Thus, endometrial DAF levels were significantly lower in the spontaneous abortion group suggesting that DAF protects the semiallogenic conceptus from autologous complement cascade and low levels of DAF is responsible for spontaneous abortions in a significant number of women.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

What is claimed is:

1. A method for diagnosing a predisposition for pregnancy failure or spontaneous abortion in a pregnant patient comprising:
    (a) measuring CD55 levels in a physiological fluid in a pregnant patient, wherein the CD55 levels are measured by measuring levels of complexes formed by contacting the physiological fluid with an anti-CD55 antibody; and
    b) determining whether CD55 levels in the physiological fluid of the patient are reduced relative to CD55 levels in a pregnant female patient not at risk of pregnancy failure or spontaneous abortion, wherein reduced CD55 levels are indicative for a predisposition for pregnancy failure or spontaneous abortion.

2. The method of claim 1, wherein the anti-CD55 antibody is immobilized on a solid surface.

3. The method of claim 1, wherein the anti-CD55 antibody comprises a detectable label or a binding site for a detectable label to form detectable complexes.

4. The method of claim 3 wherein the detectable label is an enzyme label.

5. The method of claim 4 wherein the detectable label is a fluorogenic compound.

6. The method of claim 3 wherein the binding site for the detectable label is biotin, avidin or streptavidin.

7. The method of claim 3 wherein the levels of the complexes have an optical density (OD) level below 14.

8. The method of claim 7 wherein the OD level is below 10.

9. A method for diagnosing a predisposition for pregnancy failure, spontaneous abortion or premature birth in a pregnant patient comprising:
    (a) providing a sample obtained by contacting a physiological fluid from the patient, wherein the fluid potentially comprises a CRP from the patient, with a solid surface having immobilized thereon anti-CD55 antibodies, so that CRP present in the fluid binds to the anti-CD55 antibodies;
    (b) contacting the sample with labelled CD55, which comprises a detectable label or a binding site for a detectable label, so that the labeled CD55 binds to free antibodies on the solid surface to form detectable complexes; and
    (c) detecting the complexes, wherein the quantity of the complexes is inversely proportional to the amount of CD55 in the physiological fluid, and wherein a reduced quantity of CD55-antibody complexes in the patient relative to a corresponding control is indicative for a predisposition for pregnancy failure, spontaneous abortion or premature birth.

10. The method of claim 9 wherein the detectable label is an enzyme label.

11. The method of claim 9 wherein the detectable label is a fluorogenic compound.

12. The method of claim 9 wherein the binding site for the detectable label is biotin, avidin or streptavidin.

* * * * *